United States Patent [19]

Smith Morse et al.

[11] Patent Number: 5,259,971
[45] Date of Patent: Nov. 9, 1993

[54] METHOD OF PREPARING FIBRINOGEN

[75] Inventors: Brenda Smith Morse, Chamblee, Ga.; Henry B. Kopf, Cary, N.C.

[73] Assignee: CryoLife, Inc., Marietta, Ga.

[21] Appl. No.: 844,174

[22] Filed: Mar. 2, 1992

[51] Int. Cl.⁵ .............................................. B01D 61/00
[52] U.S. Cl. ..................................... 210/650; 210/651;
210/653; 210/702; 210/806; 436/177; 436/178;
514/2; 530/382; 530/412; 530/414; 530/418
[58] Field of Search ............... 210/645, 650, 651, 653,
210/767, 806, 929, 702, 723; 422/1, 44, 101;
436/16, 176, 177; 514/2; 530/412, 414, 382, 418

[56] References Cited

U.S. PATENT DOCUMENTS

| | | | |
|---|---|---|---|
| 4,022,758 | 5/1977 | Andersson et al. | 530/382 |
| 4,210,580 | 7/1980 | Amrani | 530/382 |
| 4,278,592 | 7/1981 | Seufert | 422/44 |
| 4,333,870 | 6/1982 | Koyoma et al. | 530/414 |
| 4,420,425 | 12/1983 | Lawhon | 530/414 |
| 4,739,039 | 4/1988 | Vasquez et al. | 514/2 |

*Primary Examiner*—Robert A. Dawson
*Assistant Examiner*—Sun Uk Kim
*Attorney, Agent, or Firm*—Nixon & Vanderhye

[57] ABSTRACT

The present invention relates to a method of purifying native, intact fibrinogen from a liquid sample containing contaminants having molecular weights higher and/or lower than that of the fibrinogen. The method comprises subjecting the sample to filtration using one or more filters having a molecular weight cut-off such that the native, intact fibrinogen is separated from the contaminants.

7 Claims, 5 Drawing Sheets

METHOD OF PREPARING FIBRINOGEN

BACKGROUND OF THE INVENTION

Field of the Invention

The present invention relates, in general, to a method of preparing fibrinogen, and, in particular, to a method of fibrinogen preparation that utilizes one or more filters to separate native fibrinogen from contaminants.

Description of the Related Art

Since the middle of the 17th Century, fibrinogen has been studied as an important component of blood and a key factor in the process of coagulation. The purified protein has been studied intensively to understand the basic mechanism of clot formation. More recently, fibrinogen has been used clinically in surgery as a major component in fibrin sealant, a bioadhesive with hemostatic and healing properties.

Traditional methods for fibrinogen purification include precipitation with alcohol, salts (for example, sodium chloride, ammonium sulfate), amino acids (for example, glycine, beta-alanine), polymers (hydroxyethyl starch, polyethylene glycol) and low ionic strength solutions (Blomback et al, *Arkiv for Kemi*, band 10 nr 29, pg 415 (1956); Vila et al, *Thrombosis Research* 39:651 (1985); Siedentop et al, *Laryngoscope* 96:1062 (1986); and Leavis et al, *Arch. Biochem. Biophys.* 161:671 (1974)). Although fibrinogen can be precipitated readily using a wide variety of agents, a number of contaminating proteins co-precipitate with it (Furlan, M. "Purification of Fibrinogen" in *Curr. Probl. Clin. Biochem.* 14;133 (1984)).

When plasma is used as source material, the purification of fibrinogen to greater than 90% homogeneity usually involves several steps, is time consuming, and produces relatively low yields (50% or less) of intact native fibrinogen. The precipitation of fibrinogen by the freeze-thaw process (cryoprecipitation) usually results in low yields and contamination by other cold-insoluble proteins (*American Association of Blood Banks Technical Manual*, p. 47 (1990)).

The purification of fibrinogen for clinical use in humans requires that the process conform to the Food and Drug Administration's code for good manufacturing practice (GMP). A preferred method minimizes human manipulation of the product and involves steps which can be conducted in a sterile fashion. The above methods usually require numerous additions and transfers of solutions to obtain a pure product.

SUMMARY OF THE INVENTION

It is a general object of the invention to provide a simple, rapid method of purifying fibrinogen.

The foregoing and other objects of the invention are realized by providing a method of purifying fibrinogen wherein one or more filters are used to separate intact native fibrinogen from contaminants.

The present invention provides a unique method of fibrinogen preparation which can result in yields of intact native fibrinogen of about 85%. The method of the invention is easily adapted for small laboratory scale production (one liter or less of plasma, dissolved chemical precipitate or cryoprecipitate) or for large scale manufacturing (greater than one liter).

Other objects, features and characteristics of the present invention, as well as the methods of operation and functions of the related elements of the structure, will become more apparent upon consideration of the following detailed description and the appended claims with reference to the accompanying drawings all of which form a part of this specification, wherein like reference numerals designate corresponding parts in the various figures.

BRIEF DESCRIPTION OF THE DRAWINGS

A more complete appreciation of the present invention and many of the advantages thereof will be readily understood by reference to the following detailed description when considered in connection with the accompanying drawings in which.

Fresh frozen plasma was thawed, treated with solvent/detergent to inactivate infectious agents, and precipitated with 10% ethanol. The precipitate was redissolved in 0.02 M Tris, 0.055 M citrate, 0.022 M lysine buffer, pH 6.8, and filtered using an A/G UFP 500-E-6 hollow fiber filter. A denaturing polyacrylamide gel (3–17%) was run as follows:

| | |
|---|---|
| Lane 1 | 10% ethanol plasma fraction (pre-filtration). |
| Lanes 2–4 | Permeate fractions from filtration step containing small molecular weight contaminants (<300,000 daltons). Protein concentration of permeate decreases with time. Lanes 2 → 3 → 4. |
| Lane 5 | Molecular weight markers (from top: 200,000, 116,250, 97,400, 66,200 42,699 daltons). |
| Lane 6 | Post-filtration retentate (filter-treated fibrinogen). |
| Lanes 7–9 | Permeate fractions. |

Figure 2:
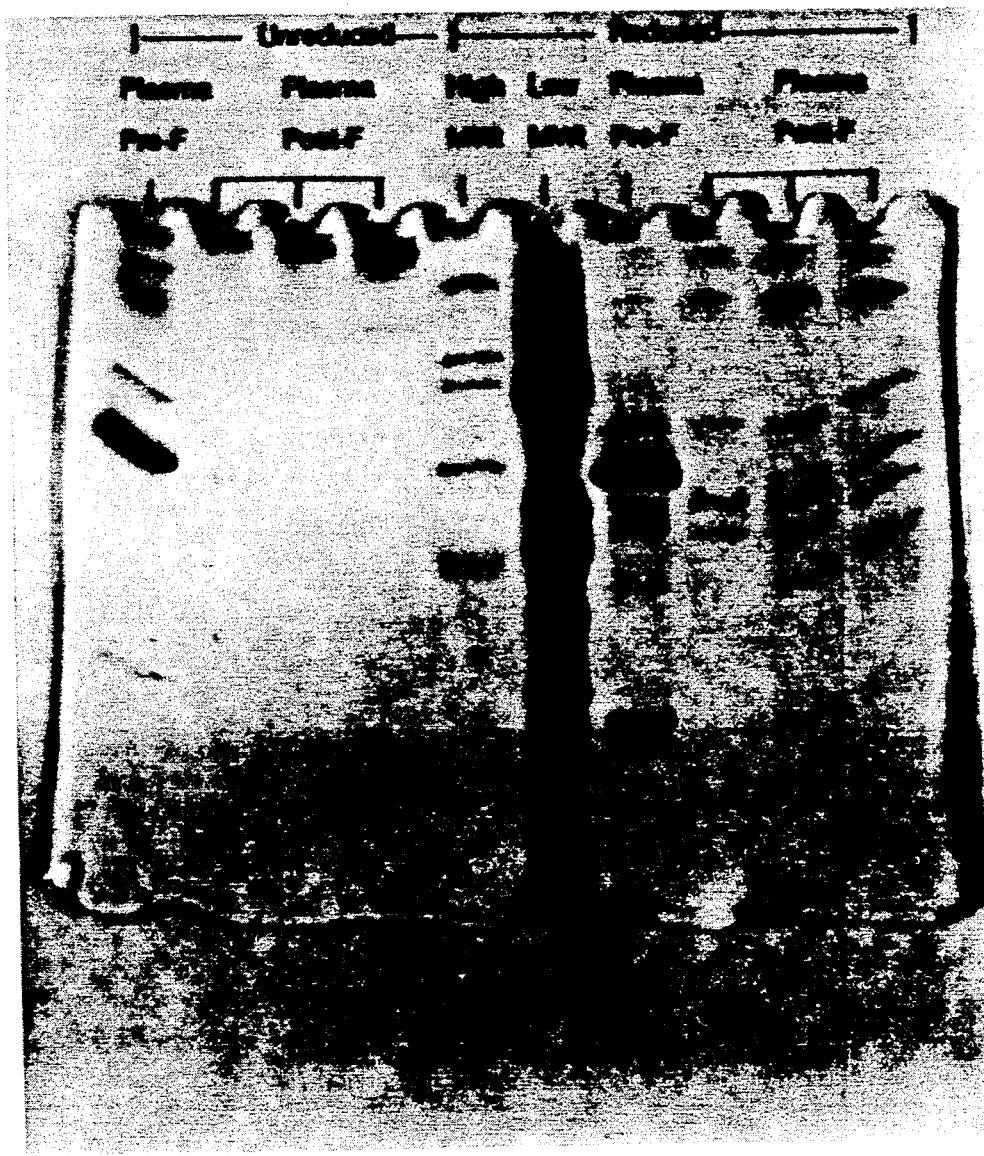

FIG. 2—Filtration of Plasma.

Fresh frozen human plasma was thawed, treated with solvent/detergent to inactivate infectious agents, and filtered using an A/G UFP 500-E-6 hollow fiber filter.

| | |
|---|---|
| Lane 1 | Solvent/detergent-treated plasma (pre-filtration). |
| Lanes 2–4 | Post-filtration Retentate (Filter-treated fibrinogen). |
| Lane 5 | Molecular weight markers (from top: 200,000, 116,250, 97,400, 66,200, 42,699 daltons). |
| Lane 7 | Solvent/detergent-treated plasma (pre-filtration). |
| Lanes 8–9 | Post-filtration retentate (filter-treated fibrinogen). |

Figure 3:
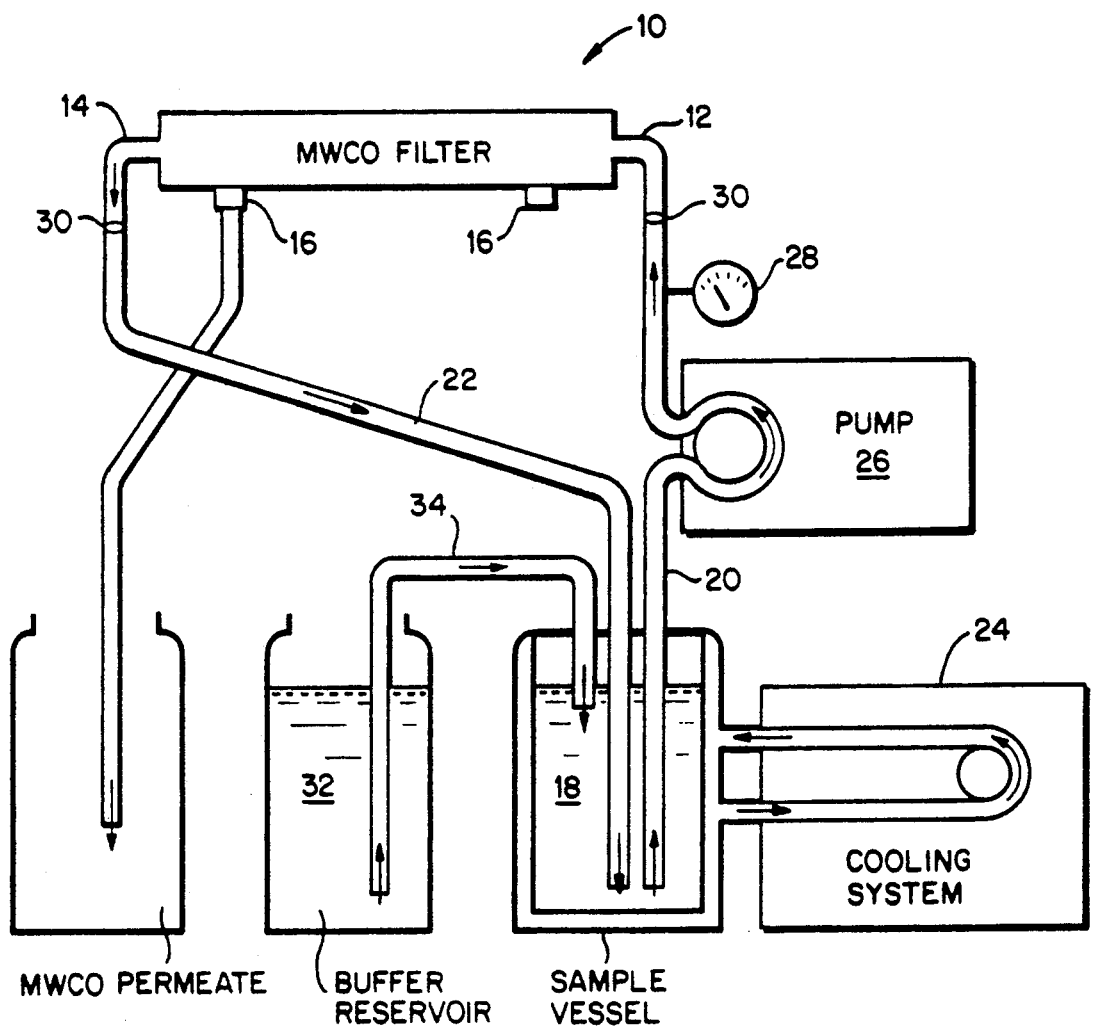
Figure 4:
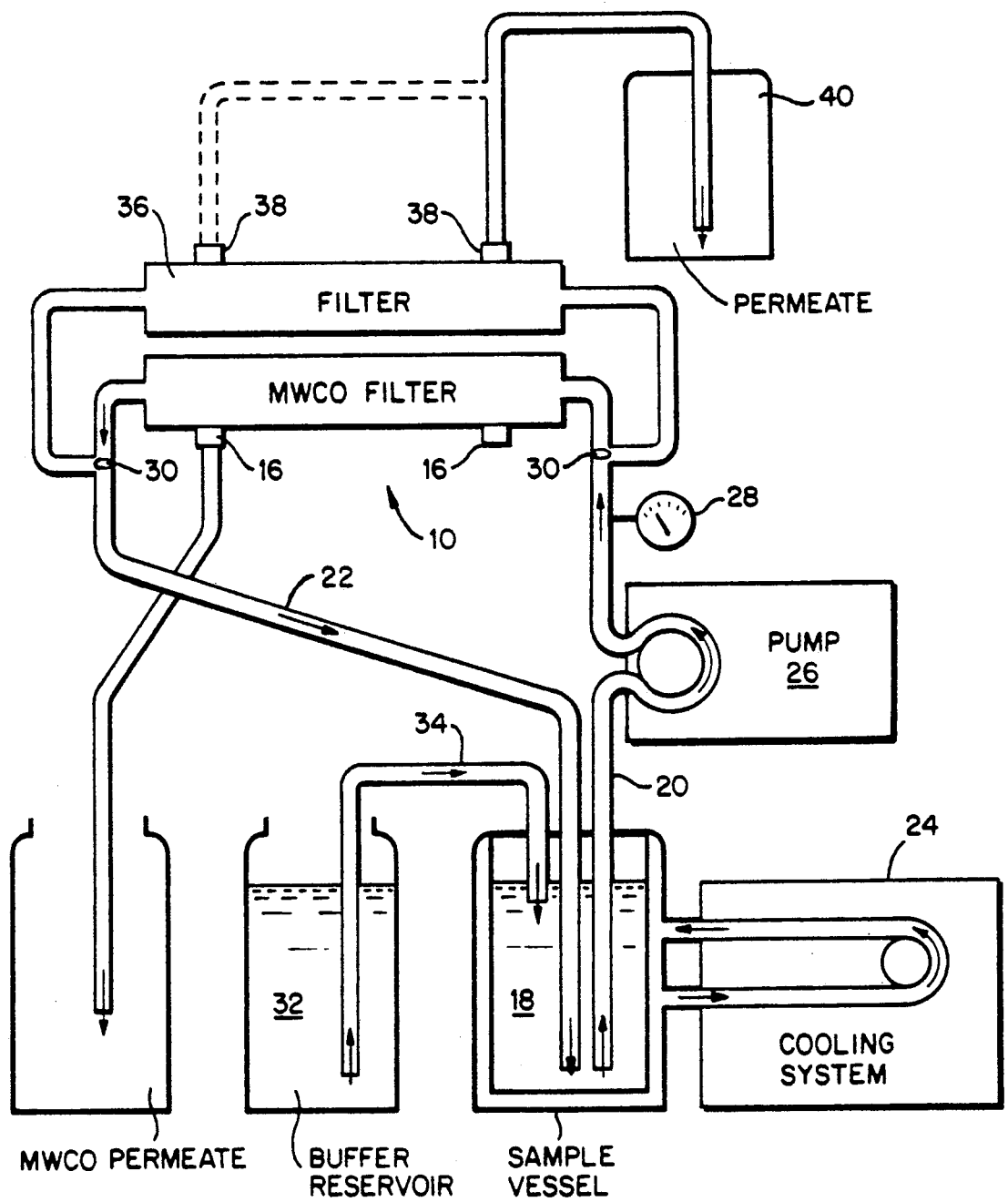
Figure 5:
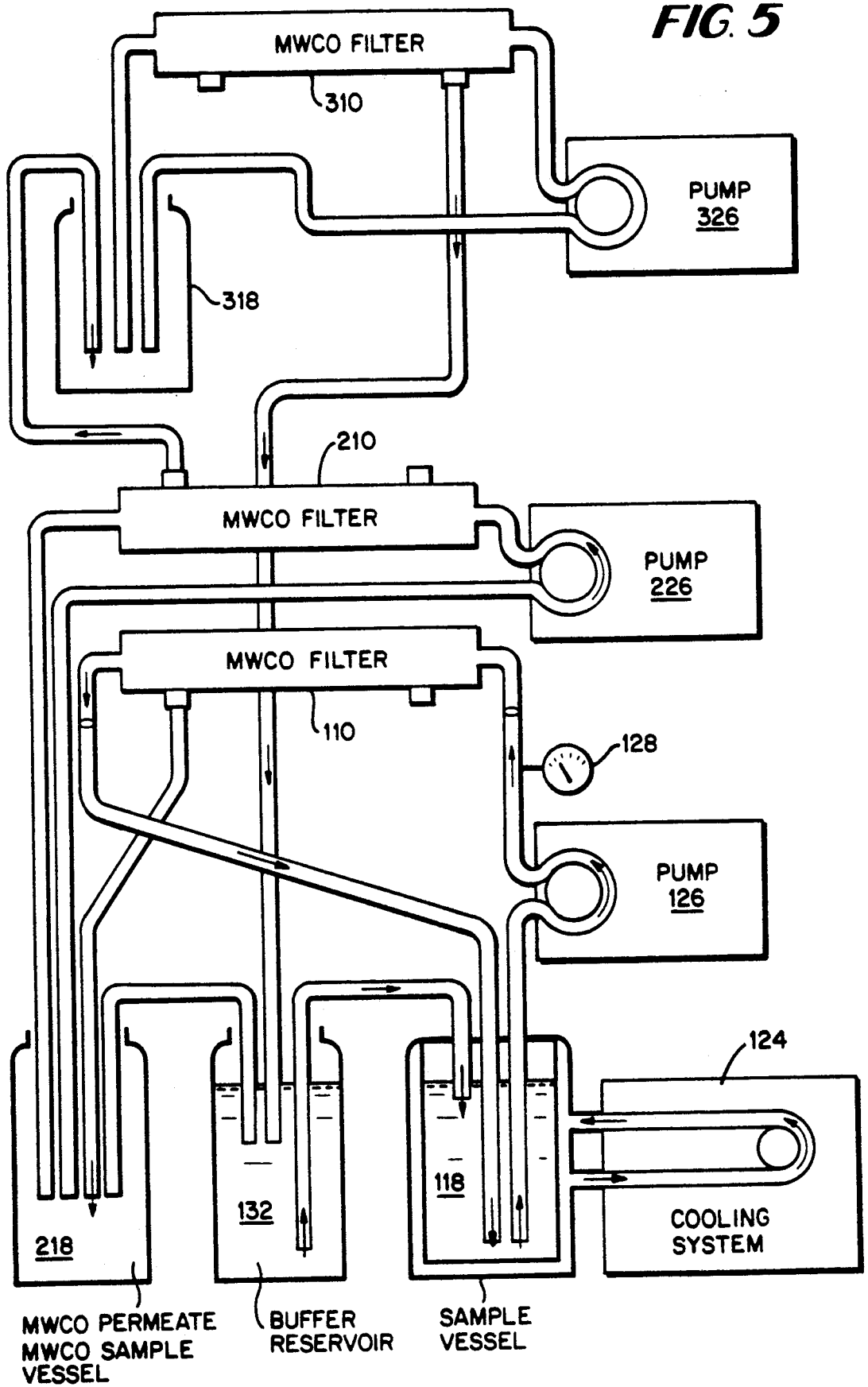

FIG. 3 is a schematic of a filtration apparatus containing a molecular weight cut-off filter;

FIG. 4 is a schematic of the filtration apparatus containing a molecular weight cut-off filter and a 0.2 micron filter for sterilization of the product; and FIG. 5 is a schematic of an alternate filtration apparatus with:

a. 3,000,000 molecular weight—0.1 micron MWCO filter for removing proteins larger than fibrinogen. Fibrinogen passes through filter with permeate b. 300,000–500,000 MWCO filter. Fibrinogen is retained and smaller proteins are passed with permeate. Permeate is carried through to c. 5,000 MWCO filter where proteins are retained and "cleansed" buffer recycled into buffer vessel.

DETAILED DESCRIPTION OF THE PRESENTLY PREFERRED EXEMPLARY EMBODIMENTS

The present invention relates to a method of purifying fibrinogen. The method comprises contacting a fibrinogen-containing liquid sample with a filter under conditions such that intact, native fibrinogen present in the sample is separated from more globular shaped and/or smaller contaminants also present in the sample but which pass through the filter.

Filters suitable for use in the present method include those capable of trapping molecules having a rod-like structure and a molecular weight of at least 120,000, preferably about 300,000, while permitting smaller and/or more globular shaped molecules to pass through. Filters having molecular weight cut-offs in the range of about 100,000 to 1,000,000 are preferred, those having molecular weight cut-offs of about 300,000 to 500,000 are most preferred. Filters can be comprised for example, of polysulfone. Advantageously, the filters are tangential flow filters with hollow fiber filters being preferred.

Using the method of the invention, fibrinogen can be purified from various sources, including biological fluids, such as single or pooled source plasma. When plasma is used, filtration can be effected directly or, preferably, following cryoprecipitation or chemical precipitation using agents such as ethanol (advantageously, 8–10% v/v) (Cohn et al, *J. Amer. Chem. Soc.* 68:459 (1946); Burnouf-Radosevich et al, Biochemical and Physical Properties of a Solvent - Detergent-Treated Fibrin Glue, *Vox Sanguinis* 58:77–84 (1990)). One skilled in the art will appreciate that while ethanol is preferred, other precipitating agents can be used such as glycine, beta-alanine, ammonium sulfate, polyvinylpyrrolidone, and hydroxyethyl starch.

In order to optimize yields, the source sample or chemically precipitated fraction thereof, can be diluted to about 2 mg/ml or less.] During the filtration process, dilution of the source sample can be made periodically, or, alternatively, dilution to a substantially fixed volume can be continuous, as noted more particularly below. One skilled in the art will appreciate that the pressure, filtration rate and the temperature of the filtration system can be optimized so as to maximize efficiency (including flow rate) of the filtration process.

The progress of the filtration process can be monitored using a variety of means capable of detecting contaminant concentration in the permeate; however, measurement of protein concentration in the permeate by determining optical density at 280 nm and purity by 3–17% polyacrylamide gel electrophoresis is preferred. Purification is essentially complete when the optical density of the permeate is less than about 0.05, preferably 0.01.

When purification has been completed, the sample can be filter sterilized using a 0.2 micron filter, as detailed below. [Optimally, the fibrinogen is present at a concentration of 2 mg/ml or less.] In addition, the purified fibrinogen can be precipitated using chemical agents (for example, 8–10% ethanol) followed by centrifugation or lyophilization. The sample can be concentrated further by continued filtration in the absence of further dilution.

Where necessary, viruses in the plasma can be inactivated using standard methods (for example, the solvent-detergent system (Piet et al, *Transfusion* 30(7) p. 591–598 (1990)) before or after the purification process.

Certain aspects of the present invention are described in greater detail by way of the following non-limiting Example. The numerals refer to the attached Figures.

EXAMPLES

Blood is obtained from a human or animal and the plasma separated from the red blood cells using a standard method. Alternatively, frozen plasma or fresh plasmapheresed plasma is used as the source of fibrinogen.

EXAMPLE 1

Filtration of Fractionated, Inactivated Plasma

Previously frozen plasma (728 ml) is thawed and subjected to an inactivation protocol. Tri-n-butyl phosphate and Tween 80 are added to the thawed plasma to a final concentration of 1% and the mixture is incubated at 30° C. for 4 hours. The solution is then chilled to 0°–4° C.

Cold USP grade ethanol is added with mixing to chilled plasma to a final concentration of 8–10%. The solution is kept in an ice bath for 30 minutes and transferred to 4° C. for 1 to 24 hours. The solution is centrifuged at 3500 rpm in a Sorval RC3 for 15 minutes and the supernatant is discarded. The pellet is redissolved in 250 ml buffer (0.05 M Tris, 0.15 M sodium chloride, 0.01 M citrate, pH 7.0) to 1–2 mg/ml The fibrinogen collecting apparatus includes a filter housing 10 having a molecular weight cut-off hollow fiber filter. (See, for example, FIG. 4.) In this example, an A/G 500,000 molecular weight cut-off filter is used. The filter housing 10 has a sample inlet 12, a return outlet 14, and at least one outlet 16 for permeate A closed sample vessel 18 is coupled via a first fluid flow conduit 20 to the inlet 12 of the filter housing 10 and via a second fluid flow conduit 22 to the outlet 14 of the filter housing 10. The fluid disposed within the sample vessel 18 is continuously cooled. As illustrated, such cooling may be accomplished by conducting the sample fluid to a cooling system 24, for example, an ice bath, so that there is a continuous cooling and circulation of the sample.

A pump, for example a peristaltic pump 26, is operatively coupled to the first fluid flow conduit 20 to positively convey fluid through that conduit from the sample vessel 18 to the filter housing 10. A pressure gage 28 is preferably mounted downstream from the pump 26 to monitor the pressure of the fluid on the inlet side of the filter housing 10.

A clamp 30 is mounted to each of the fluid flow conduits adjacent the filter housing to allow flow to be selectively cut-off. In the alternative, a valve can be mounted in-line to selectively cut-off or divert flow as desired.

Buffer can be intermittently added to the sample vessel 18 to replace the collected permeate. In the alternative and preferably, buffer is continuously added to the sample vessel 18 from a buffer reservoir 32 through a suitably disposed fluid flow conduit 34 which may be equipped with a pump mechanism (not shown).

The apparatus is preferably pre-chilled by running cold buffer through it for approximately 15–30 minutes. The cold fibrinogen faction (about 500 ml at 1.0 mg/ml fibrinogen) is then added to the sample vessel 18. The sample is continuously chilled by re-circulating through the cooling system 24. The chilling process is continued throughout the filtration separation process. Filtration is initiated and the pump speed adjusted so that the inlet pressure is less than 5 pounds per square inch.

The fluid level in the sample vessel 18 is maintained throughout filtration by conveying buffer from the buffer reservoir 32 to the sample vessel 18. In the alternative, as noted above, buffer can be periodically added. After filtration has been initiated and the pressure adjusted as noted above, permeate is collected for analysis and then discarded. The circulating solution or retentate is collected in the sample vessel 18 through the second conduit 14. If the filter becomes clogged, it can be periodically washed with about 200-500 ml of buffer and the wash solution combined with the sample. About 7 liters of buffer are generally necessary to achieve purification before further processing of the collected fibrinogen.

After the fibrinogen has been purified, the sample can be sterilized. More particularly, once purification has been achieved and sterilization is desired, the inlet and outlet ports of the cut-off filter housing are closed and sample flow is diverted through a polypropylene 0.2 micron filter housing 36 mounted in parallel flow relation to the cut-off filter housing 10. For that reason a diverter valve or a Y-connector and clamp combination can be provided rather than a tube clamp 30. The purified sample is then circulated through the 0.2 micron filter. At least one permeate outlet 38 is defined in the filter housing 36 so that sterilized permeate can be collected. The fluid volume of the sample is again replaced by periodically or continuously adding buffer solution until the fibrinogen content of the retentate is negligible. Any desired buffer can be utilized during the sterilization process (e.g., 0.05 M Tris, 0.15 M sodium chloride, pH 7.0).

The sterilized fibrinogen collected in the sterilized permeate container 40 can then be concentrated by precipitation using 8% ethanol followed by centrifugation or lyophilization.

Figure 1:
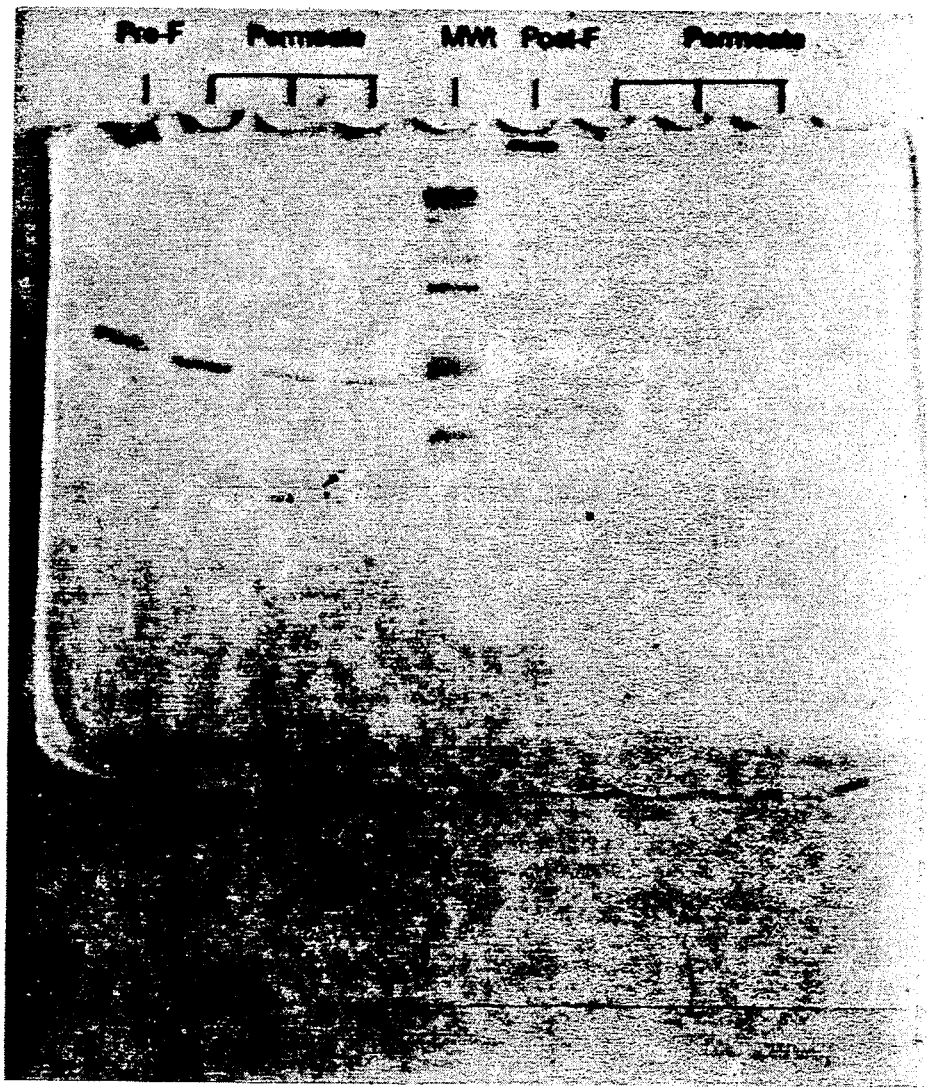
FIG. 1—Filtration of Fractionated Plasma.

The purity of the resulting preparation is determined by gel electrophoresis (FIGS. 1 and 2). The minor band at the top of the gel is fibronectin. In addition, the preparation exhibits cross-linking activity, indicating the presence of Factor XIII. By gel electrophoresis, the preparation is comparable to purified fibrinogen obtained by classical methods from a commercial supplier, KabiVitrum.

As an alternative to the apparatus shown in and described above with reference to FIGS. 3 and 4, an apparatus as shown in FIG. 5 can be used to isolate fibrinogen. This apparatus also provides for the filtering and recycling of buffer solution. Those components which are the same or similar to those of the structure of FIGS. 3 and 4 have been assigned corresponding reference numerals but a detailed explanation thereof is not necessary and is therefore omitted.

In the embodiment of FIG. 5, the sample is first conveyed from the sample container 118 to a filter housing 110 for removing proteins larger than the desired fibrinogen, for example, a 3,000,000 molecular weight cut-off filter. Fibrinogen passes through the filter with the permeate to a permeate sample vessel 218. The larger proteins are then recycled to the sample vessel 118, and buffer is gradually added from buffer container 132 to replace permeate, as described above with reference to FIGS. 3 and 4 so that, gradually, all fibrinogen is separated, although in this embodiment the desired material collects in the permeate sample vessel 218 instead of in the original sample vessel 118.

The desired, fibrinogen-rich permeate is then cycled through its own filter housing 210, e.g., having a 500,000 molecular weight cut-off filter, to separate the desired fibrinogen from smaller materials. The purified fibrinogen is recycled through the permeate sample vessel 218 and buffer is gradually added from buffer container 132 to replace the fibrinogen poor permeate, as was described with reference to FIGS. 3 and 4.

The fibrinogen-poor permeate can then be cycled from container 318 through its own filter housing 310, e.g., having a 5,000 molecular wight cut-off filter, to separate small proteins from the buffer solution. The buffer solution permeate can then be returned to the buffer reservoir 132 for reuse.

Although only schematically illustrated, each of the cyclic filter systems shown in and described with reference to FIG. 5 has its own pump or shares a pump for circulating the material being filtered through the tubing and may have a cooling system (not illustrated in detail) corresponding to systems 24 and 124, provided for the original sample container in FIGS. 3, 4 and 5.

EXAMPLE 2

Filtration of Fractionated Plasma

Previously frozen plasma (742 ml) was thawed and inactivated with 1% TNBP/Tween80 at 30° C. for 4 hours. The mixture was chilled to 0°-5° C., ethanol was added to 8-10%, and the solution incubated in an ice bath for 2 hours. The solution was centrifuged for 15 minutes in an RC3 at 3500 rpm. The pellet was resuspended in 1 L buffer (0.02 M Tris, 0.55 M citrate, 0.022 M lysine, pH 6.8) [Note: this is a preferred buffer.] Visible clumps were removed.

The system included a UFP 500-E-6 filter. Filtration was achieved in 4 hours using an inlet pressure of 2-5 PSI and a permeate flow rate of 80-85 ml/min. (see FIG. 1A). The yield of clottable protein from the filtration step was 85% and the retentate exhibited Factor XIII activity.

EXAMPLE 3

Filtration of Unfractionated Plasma

Lysine (to 0.022 M) was added to thawed plasma, the plasma was inactivated as described above and chilled. Visible clumps were removed. The system included a UFP 500-E-6 filter and a buffer containing 0.02 M Tris, 0.55 M citrate, 0.022 M lysine, pH 6.8. The system was chilled by placing the sample reservoir in an ice water bath. External filter temperature was 13°-17° C.

The purity of the retentate was 46% clottable protein. Gel electrophoresis of the unreduced retentate (see FIG. 2) indicates the majority of contaminating proteins with molecular weight less than fibrinogen had been removed; the reduced retentate exhibits contaminating protein subunits of molecular weight greater than the alpha, beta, and gamma fibrinogen subunits.

The entire contents of documents cited herein are incorporated herein by reference.

While the invention has been described in connection with what is presently considered to be the most practical and preferred embodiment, it is to be understood that the invention is not limited to the disclosed embodiment, but, on the contrary, is intended to cover various modifications and equivalent arrangements include within the spirit and scope of the appended claims.

What is claimed is:

1. A method of purifying native, intact fibrinogen from a liquid sample containing a contaminant having a molecular weight less than that of said fibrinogen, which method comprises:

subjecting said sample to filtration using a filter having a molecular weight cut-off such that said fibrinogen is retained by said filter and said contaminant passes through said filter; and removing said retained fibrinogen from said filter.

2. The method according to claim 1 wherein said liquid sample is plasma.

3. The method according to claim 1 wherein said fibrinogen is cryoprecipitated or chemically precipitated from said sample and said precipitated fibrinogen redissolved prior to said filtration.

4. The method according to claim 1, wherein said filter is a polysulfone filter.

5. The method according to claim 1, wherein said fibrinogen retained by said filter is subjected to filtration using a second filter having a molecular weight cut-off such that fibrinogen passes through said second filter and proteins having a molecular weight greater than that of fibrinogen are retained.

6. The method according to claim 1 wherein said filter has a molecular weight cut-off in the range of 100,000 to 1,000,000 daltons.

7. The method according to claim 6 wherein said filter has a molecular weight cut-off of about 500,000 daltons.

* * * * *